(12) United States Patent
Thuemen

(10) Patent No.: US 11,426,057 B2
(45) Date of Patent: Aug. 30, 2022

(54) VIDEO ENDOSCOPE HAVING FASTENER ABSORBING TORSIONAL FORCES ACTING ON SIGNAL LINE CONNECTED TO IMAGE SENSOR

(71) Applicant: OLYMPUS WINTER & IBE GMBH, Hamburg (DE)

(72) Inventor: Alrun Thuemen, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 118 days.

(21) Appl. No.: 16/957,034

(22) PCT Filed: Dec. 6, 2018

(86) PCT No.: PCT/EP2018/083836
§ 371 (c)(1),
(2) Date: Jun. 22, 2020

(87) PCT Pub. No.: WO2019/121042
PCT Pub. Date: Jun. 27, 2019

(65) Prior Publication Data
US 2020/0390317 A1    Dec. 17, 2020

(30) Foreign Application Priority Data
Dec. 22, 2017   (DE) .......................... 102017131171.8

(51) Int. Cl.
*A61B 1/00* (2006.01)
*A61B 1/05* (2006.01)
(52) U.S. Cl.
CPC ...... *A61B 1/00121* (2013.01); *A61B 1/00183* (2013.01); *A61B 1/05* (2013.01); *A61B 1/051* (2013.01); *A61B 2562/166* (2013.01)

(58) Field of Classification Search
None
See application file for complete search history.

(56) References Cited

U.S. PATENT DOCUMENTS 5,689,365 A    11/1997 Takahashi
6,030,339 A *  2/2000 Tatsuno ............. A61B 1/00195
                                              600/112
(Continued)

FOREIGN PATENT DOCUMENTS

DE    102004023866 B3    2/2006
DE    102007009282 A1    8/2007
(Continued)

OTHER PUBLICATIONS

International Search Report dated Dec. 2, 2019 issued in PCT/EP2018/083836.
German OA dated Oct. 22, 2018 issued in DE 102017131171.8.

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

A video endoscope including an elongate shaft having a distal end and a proximal end; a tubular sleeve arranged in the shaft so as to be rotatable about a longitudinal axis of the shaft; a connector arranged at the proximal end of the shaft; an objective arranged at the distal end of the shaft; at least one image sensor arranged in the shaft so as to be proximal to the objective, the at least one image sensor being surrounded by the tubular sleeve; a flexible signal line connecting the at least one image sensor to the connector; and a fastener for detachable fastening the flexible signal line.

10 Claims, 3 Drawing Sheets

(56) References Cited

U.S. PATENT DOCUMENTS

| | | | |
|---|---|---|---|
| 6,464,631 B1 * | 10/2002 | Girke | A61B 1/05 600/137 |
| 10,524,649 B2 | 1/2020 | Wieters et al. | |
| 2008/0108869 A1 * | 5/2008 | Sanders | A61B 1/00124 600/109 |
| 2013/0023770 A1 * | 1/2013 | Courtney | A61B 17/320758 600/478 |
| 2014/0288369 A1 * | 9/2014 | Henley | A61B 1/00179 600/109 |
| 2015/0271370 A1 * | 9/2015 | Henley | A61B 1/051 348/76 |
| 2017/0006264 A1 * | 1/2017 | Tomatsu | A61B 1/0669 |
| 2017/0078583 A1 * | 3/2017 | Haggerty | A61B 1/00071 |
| 2017/0105612 A1 | 4/2017 | Wieters et al. | |
| 2021/0145257 A1 * | 5/2021 | Levinson | A61B 1/00121 |

FOREIGN PATENT DOCUMENTS

| | | |
|---|---|---|
| DE | 102007009292 A1 | 8/2008 |
| DE | 102012017589 A1 | 3/2014 |
| DE | 102014209980 A1 | 11/2015 |
| DE | 102014212712 A1 | 1/2016 |
| EP | 1997421 A1 | 12/2008 |
| WO | WO 2016/000974 A1 | 1/2016 |

* cited by examiner

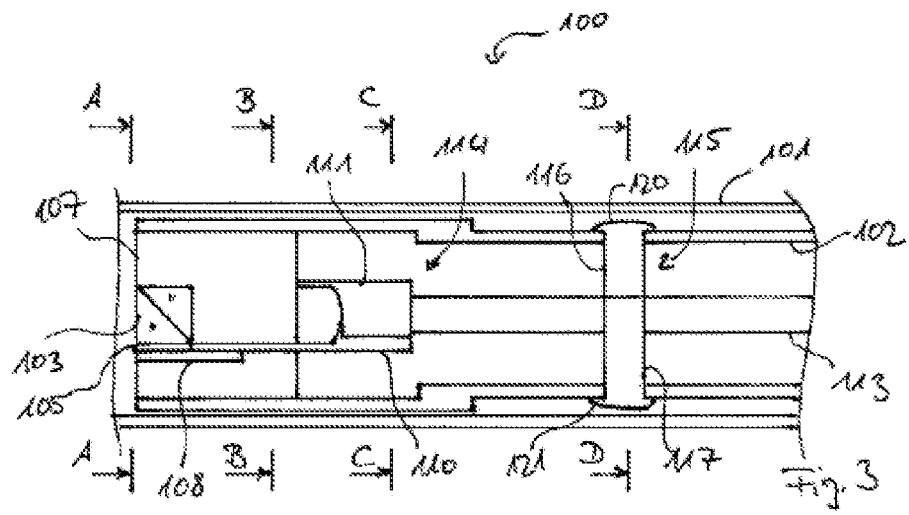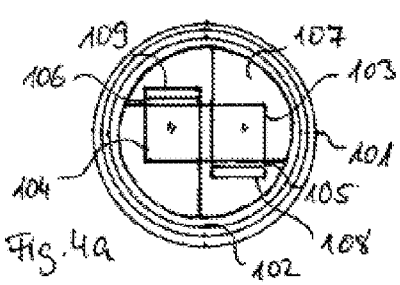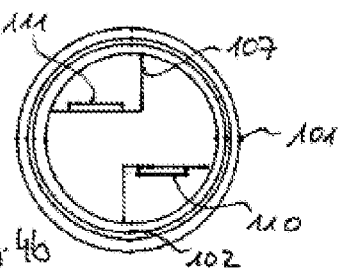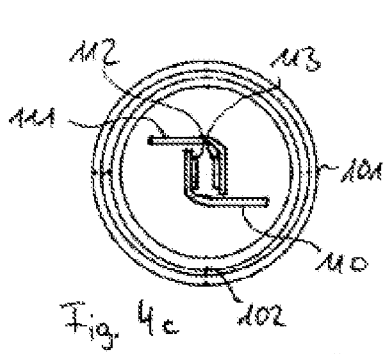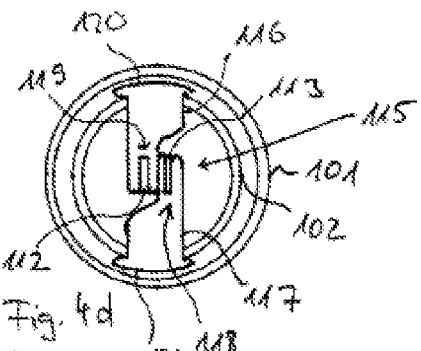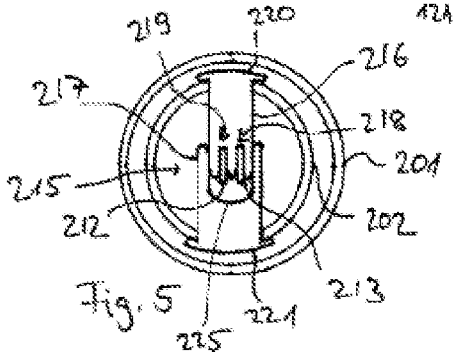

VIDEO ENDOSCOPE HAVING FASTENER ABSORBING TORSIONAL FORCES ACTING ON SIGNAL LINE CONNECTED TO IMAGE SENSOR

CROSS-REFERENCE TO RELATED APPLICATION

The present application is based upon and claims the benefit of priority from PCT/EP2018/083836 filed on Dec. 6, 2018, which claims benefit to DE 10 2017 131 171.8 filed on Dec. 22, 2017, the entire contents of each of which are incorporated herein by reference.

BACKGROUND

Field

The present disclosure relates to a video endoscope and more particularly to a video endoscope comprising an elongate shaft having a distal end and a proximal end, an objective that is arranged at the distal end of the shaft, as well as at least one image converter that is arranged in the shaft so as to be proximal to the objective, the at least one image converter being surrounded by a tubular sleeve which is arranged in the shaft so as to be rotatable about a longitudinal axis of the shaft, and the at least one image converter being connected to a connection element, arranged at the proximal end of the shaft, by means of a flexible signal line.

Prior Art

Video endoscopes are used in medicine and in technology in order to examine cavities that are difficult to access. For this purpose, endoscopes comprise an elongate shaft having a proximal end, i.e. arranged close to the user, and a distal end, i.e. remote from the user. In this case, the shaft may be flexible or rigid.

An objective is arranged at the distal end of the shaft, which objective projects an image of the cavity to be examined onto an electronic image converter. The image converter converts said image into electrical video signals. The image converter can be a CCD or CMOS chip for example.

The video signals generated by the image converter are conducted to the proximal end of the shaft via a signal line, at which end they are output via a connection element, optionally after electronic pre-processing.

If the endoscope shaft is rotated about the longitudinal axis thereof during use, for example in order to achieve a better viewing angle with respect to a detail of interest, the horizon of a video image reproduced from the video data rotates. As a result, it is more difficult for the user of the video endoscope to orient themselves with respect to the video image. This problem is even greater if the video endoscope has a lateral or even variable viewing direction.

In order to provide a remedy, the image converter is often mounted in the shaft so as to be rotatable about the longitudinal axis of the shaft. For this purpose, the image converter is fastened in a tubular sleeve which is in turn rotatably mounted in the shaft. The rotation of the sleeve can be achieved for example by means of a magnetic coupling which transfers the rotation of a swivel, arranged outside the shaft, via the shaft, to the tubular sleeve.

The connection element at the proximal end of the shaft is generally connected to the proximal end of the shaft in a hermetically sealing manner, and thus cannot rotate together with the tubular sleeve. Therefore, a flexible signal line is used between the image converter and the connection element.

A corresponding video endoscope is known for example from DE102007009292 A1.

Corresponding video endoscopes are problematic in that the flexible signal line is subjected to various mechanical stresses. These are tensile and/or compression forces which act in the longitudinal direction of the shaft and may result from different thermal expansion of the individual components. In addition, torsional forces arise when the tubular sleeve is rotated in the shaft.

The corresponding forces act on the connection point of the signal line to the image converter or to further circuits connected to the image converter. Since connection points of this kind are small and sensitive, owing to the restricted space conditions at the distal end of a video endoscope, there is the risk of the connection points being damaged. As a result, in the most unfavorable case the video endoscope becomes unusable.

SUMMARY

An object is therefore that of providing a video endoscope which is improved with respect to the problem described above.

Such object can be achieved by a video endoscope, comprising an elongate shaft having a distal end and a proximal end, an objective that is arranged at the distal end of the shaft, as well as at least one image converter that is arranged in the shaft so as to be proximal to the objective, the at least one image converter being surrounded by a tubular sleeve which is arranged in the shaft so as to be rotatable about a longitudinal axis of the shaft, and the at least one image converter being connected to a connection element, arranged at the proximal end of the shaft, by means of a flexible signal line, which video endoscope is developed in that the flexible signal line is detachably fastened in the tubular sleeve by means of a position-securing element. As a result of the fastening of the signal line in the tubular sleeve, the forces acting on the signal line are conducted away via the position-securing element, into the tubular sleeve, without stressing connection points of the signal line at the distal end of the shaft. The risk of damage to the connection points can thus be almost entirely excluded.

The flexible signal line can comprise a flexible printed circuit board. Flexible printed circuit boards are simpler to connect than cables, for example, and at the same time exhibit more uniform bending behavior.

A video endoscope can comprise two image converters which are arranged in a common tubular sleeve. Two image converters are used in 3D video endoscopes for example, in order to allow for stereo endoscopic pictures. In the case of 3D video endoscopes of this kind, the connection points of the image converter to the signal lines are particularly sensitive owing to the restricted installation space.

Accordingly, the flexible signal line of a corresponding video endoscope can comprise a separate flexible printed circuit board for each image converter.

The position-securing element can be inserted into the tubular sleeve from the outside. As a result, the position-securing element can be introduced in a particularly simple manner, following the connection of the flexible signal line to the image converter, in order to fix the signal line.

The position-securing element can comprise a slit-like receptacle for the at least one flexible printed circuit board.

The position-securing element can then be inserted into the tubular sleeve such that the slit-like receptacle glides over the flexible printed circuit board and fixed said circuit board in the process.

The position-securing element can comprise two subcomponents which can undergo reciprocal elastic deformation when inserted into the tubular sleeve, such that the at least one flexible printed circuit board is fastened in the slit-like receptacle by frictional engagement. In this case, it is possible, for example, for mutually opposing walls of the slit-like receptacle of a subcomponent to be pressed together by the other subcomponent, as a result of which the flexible printed circuit board is clamped between the walls.

In this case, each of the two subcomponents can comprise a slit-like receptacle for a flexible printed circuit board. It is then possible, first of all, for the first subcomponent to be inserted into the tubular sleeve such that the slit-like receptacle of the first subcomponent overlaps a first flexible printed circuit board. Subsequently, the second subcomponent to be inserted such that the slit-like receptacle of the second subcomponent overlaps a second flexible printed circuit board.

Alternatively, one of the two subcomponents can comprise two slit-like receptacles, for one flexible printed circuit board in each case. In this case, the second subcomponent is intended only for the elastic deformation of the first subcomponent, in order to fix the flexible printed circuit board therein.

BRIEF DESCRIPTION OF THE DRAWINGS

The embodiments will be explained in the following, with reference to some drawings that are given by way of example. These drawings are intended only to improve understanding of the invention, and do not constitute a restriction of the subject matter of the invention.

In the figures:

FIG. 3 illustrates the internal structure of a further endoscope,

FIGS. 4a-4d illustrate cross-sectional views of the video endoscope according to FIG. 3, FIG. 5 illustrates a cross-sectional view through a further video endoscope.

DETAILED DESCRIPTION

Figure 1:
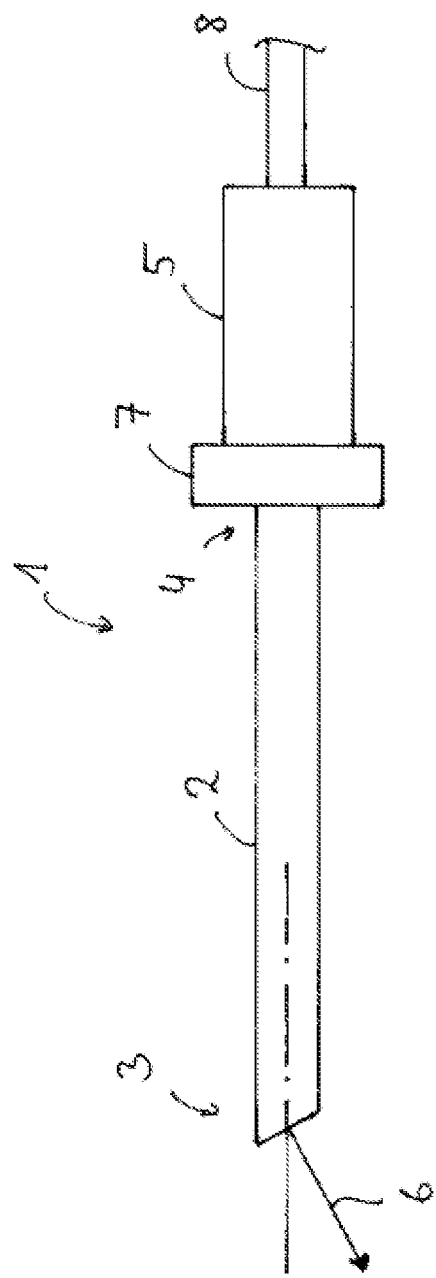
FIG. 1 illustrates a video endoscope.

FIG. 1 shows a video endoscope 1. The video endoscope 1 comprises an elongate shaft 2 having a distal end 3 and a proximal end 4. A handle 5 is arranged at the proximal end 4 of the shaft 2, by means of which the video endoscope 1 can be retained and operated.

An objective (not shown) is arranged at the distal end 3 of the shaft 2, the viewing direction of which objective is oriented in the direction of the arrow 6. Rotating the video endoscope 1 makes it possible for the viewing direction of the objective to be rotated about the longitudinal axis thereof. The swivel 7 is used for controlling the horizon of an image recorded by the video endoscope 1. The video signals generated by the video endoscope 1 are output via a cable 8.

Figure 2:
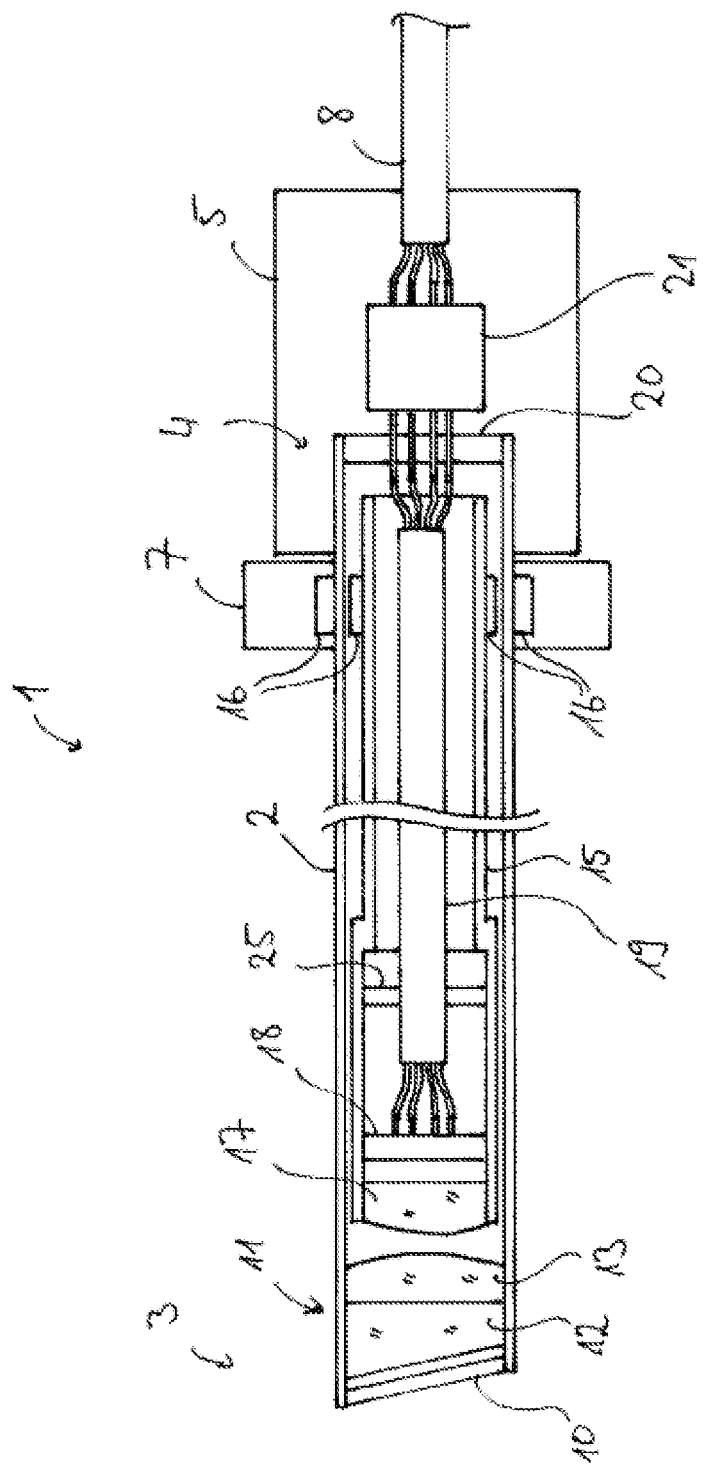
FIG. 2 illustrates the internal structure of a video endoscope.

FIG. 2 is a schematic view of the internal structure of the video endoscope 1. The distal end 3 of the shaft 2 is hermetically sealed by means of a window 10. A distal objective module 11, comprising a prism assembly 12 and a lens 13, is located behind the window 10. The distal objective module 11 is connected to the shaft 2 for conjoint rotation. Furthermore, a tubular sleeve 15 is provided in the shaft 2, which sleeve is rotatable about a longitudinal axis of the shaft 2. The tubular sleeve is coupled to the swivel 7 by means of magnets 16, such that a rotation of the swivel 7 about the longitudinal axis of the video endoscope 1 is transferred to the tubular sleeve 15.

A proximal objective part 17 and an electronic image converter 18, such as an image sensor, are fixed in the tubular sleeve 15, for conjoint rotation, at the distal end of the tubular sleeve 15. A flexible signal line 19 connects the image sensor 18 to a connection element 20 at the proximal end 4 of the shaft 2. The connection element 20 is inserted into the shaft 2 in a hermetically sealing manner.

Electrical signals of the image sensor 18 are transferred to the connection element 20 via the flexible signal line 19, and are guided out of the shaft 2 at said connection element. A signal processor 21 processes the signals and outputs them via a cable 8.

In order to adjust the viewing direction of the video endoscope, the user can rotate the handle 5. In the process, the shaft 2 rigidly connected thereto, as well as the distal objective module 11, also rotate. In order not to lose the horizon of the image in the process, the user holds the swivel 7 firmly, such that it does not rotate therewith. Accordingly, the tubular sleeve 15 together with the proximal objective module 17 and the image converter 18 likewise is not rotated, and the horizon of the recorded image remains constant.

The relative rotation between the tubular sleeve 15 and the shaft leads to torsion of the signal line 19. As a result, the connections between the signal line 19 and the image converter 18 are subjected to mechanical stress.

In order to reduce this stress, a position-securing element (fastener) 25 is provided, which element detachably fastens the signal line 19 in the tubular sleeve 15. As a result, the torsion forces in the signal line 19 are absorbed by the position-securing element 25 and passed to the tubular sleeve 15, without connection points between the signal line and the image converter being subjected to stress.

In this case, the position-securing element 25 is configured so as to be detachable, in order to allow for dismantling of the video endoscope 1, for example for maintenance purposes.

The connection points between the signal line 19 and the connection element 20 are likewise stressed by the torsion of the signal line 19. However, there is significantly more installation space available in the region of the connection element 20, and therefore these connection points can be formed so as to be mechanically more stable.

FIG. 3 is a detail view of the internal structure of a further video endoscope 100. FIGS. 4a to 4d are cross-sectional views of the video endoscope shown in FIG. 3, along the planes A-A (FIG. 4a), B-B (FIG. 4b), C-C (FIG. 4c) and D-D (FIG. 4d).

The video endoscope 100, which is configured as a stereo video endoscope, again comprises a shaft 101 and a tubular sleeve 102 that is rotatably mounted in the shaft 101. Two prism blocks 103, 104 are arranged in parallel with one another, in the tubular sleeve 102, as proximal objective portions, of which only the prism block 103 is visible in FIG. 3. The prism blocks deflect light beams, emanating from a distal objective portion (not shown), by 90°, onto two image converters 105, 106, such as image sensors, of which only the image converter 105 is visible in FIG. 3.

The prism blocks 103, 104 and the image converter 105, 106 are fastened to a support element 107 which is connected to the tubular sleeve 102 for conjoint rotation. The support element 107 additionally functions as a heat sink and heat dissipator for the electrical heat loss from the image converters 105, 106.

The image sensors 105, 106 are connected to circuits 108, 109 which read out image information from the image converters 105, 106 and convert said information into video signals. The video signals are conducted to flexible signal conductors 112, 113 via transition circuit boards 110, 111, which signal conductors extend as far as the proximal end (not shown) of the shaft 101. In FIG. 3, only the signal conductor 113 of the signal conductors 112, 113 is visible. The signal conductors 112, 113 are configured as flexible printed circuit boards.

The transition circuit boards 110, 111 and the signal conductors 112, 113 each carry a plurality of individual strip conductors which are not shown, for the sake of clarity. In one connection region 114 the strip conductors of the signal conductors 112, 113 are connected to the strip conductors of the transition circuit board 110, 111 by means of soldered joints.

In the proximal region thereof, the transition circuit boards 110, 111 are angled towards the longitudinal axis of the video endoscope 100 by an angle of approximately 90°. As a result, the signal conductors 112, 113 can be arranged as closely as possible to the longitudinal axis of the video endoscope 100.

If the sleeve 102 is rotated in the shaft 101, the signal conductors 112, 113 are twisted. In order to prevent the resulting torsion forces from damaging the solder points in the connection region 114, the signal conductors 112, 113 are fixed proximally of the connection region 114, by means of a position-securing element 115. The position-securing element 115 consists of two subcomponents 116, 117 which are inserted into the sleeve 102 from opposing sides.

The subcomponents 116, 117 each comprise a slit-like receptacle 118, 119 which each receive one of the signal conductors 112, 113, respectively. In this case, the subcomponents 116, 117 are configured such that they undergo reciprocal elastic deformation when inserted into the sleeve 102. As a result, the signal conductors 112, 113 are fixed in the slit-like receptacles 118, 119 by frictional engagement.

At the outer ends thereof, the subcomponents 116, 117 comprise mushroom-shaped extensions 120, 121 which both prevent the subcomponents 116, 117 from being pushed too deeply into the sleeve 102, and facilitate removal of the subcomponents 116, 117 from the sleeve 102 when the video endoscope 100 is to be dismantled for maintenance or repair purposes.

The subcomponents 116, 117 can for example be produced from a plastics material, in an injection molding process. In this case, the plastics material should be as unabrasive as possible, in order to prevent damage to the signal conductors 112, 113 during assembly or dismantling of the video endoscope 100.

FIG. 5 is a cross-sectional view of a further video endoscope 200 which largely corresponds to the video endoscope 100. In this case, FIG. 5 is a cross section through a plane that corresponds to the plane D-D in FIG. 3. Mutually corresponding elements are provided, in the figures, with a reference sign increased by 100, and will not be explained in detail again.

The video endoscope 200 differs from the video endoscope 100 in that in this case the subcomponent 216 comprises two slit-like receptacles 218, 219 which receive the signal conductors 212, 213. The subcomponent 217, in contrast, comprises a wide receptacle 225 which surrounds the entire subcomponent 216 and thus fixes the signal conductors 212, 213 by frictional engagement.

What is claimed is:

1. A video endoscope comprising:
    an elongate sealed shaft having a distal end and a proximal end;
    a tubular sleeve arranged in the shaft so as to be rotatable within the shaft about a longitudinal axis of the shaft;
    a connector arranged at the proximal end of the shaft;
    an objective arranged at the distal end of the shaft;
    at least one image sensor arranged in the tubular sleeve so as to be proximal to the objective, the at least one image sensor being surrounded by the tubular sleeve;
    a flexible signal line connecting the at least one image sensor to the connector; and
    a fastener disposed proximally to the image sensor, the fastener being configured to detachably fasten the flexible signal line to the tubular sleeve to absorb torsional forces acting on the signal line due to the rotation of the tubular sleeve within the shaft.

2. The video endoscope according to claim 1, wherein the flexible signal line comprises at least one flexible printed circuit board.

3. The video endoscope according to claim 2, wherein the fastener comprises a slit-like receptacle for the at least one flexible printed circuit board.

4. The video endoscope according to claim 3, wherein the fastener comprises two subcomponents which undergo reciprocal elastic deformation when inserted into the tubular sleeve such that the at least one flexible printed circuit board is fastened in the slit-like receptacle by frictional engagement.

5. The video endoscope according to claim 4, wherein each of the two subcomponents comprises a slit-like receptacle for the at least one flexible printed circuit board.

6. The video endoscope according to claim 4, wherein the at least one flexible printed circuit board comprises two flexible printed circuit boards and one of the two subcomponents comprises two slit-like receptacles for the two flexible printed circuit boards, respectively.

7. The video endoscope according to claim 1, wherein the at least one image sensor comprises two image sensors arranged in the tubular sleeve.

8. The video endoscope according to claim 7, wherein the flexible signal line comprises a flexible printed circuit board for each image sensor.

9. The video endoscope according to claim 1, wherein the fastener is configured to be inserted into the tubular sleeve from an exterior of the tubular sleeve.

10. The video endoscope according to claim 1, further comprising a magnetic coupling between the shaft and the tubular sleeve to rotate the tubular sleeve within the shaft.

* * * * *